United States Patent [19]

Bresina

[11] Patent Number: 5,741,256
[45] Date of Patent: Apr. 21, 1998

US005741256A

[54] HELICAL OSTEOSYNTHETIC IMPLANT

[75] Inventor: Stephen Bresina, Davos Platz, Switzerland

[73] Assignee: Synthes (U.S.A.), Paoli, Pa.

[21] Appl. No.: 782,231

[22] Filed: Jan. 13, 1997

[51] Int. Cl.[6] .................................................. A61B 17/78
[52] U.S. Cl. .......................................... 606/62; 606/67
[58] Field of Search ................................. 606/67, 68, 65, 606/66, 62, 63, 64, 72, 73, 60

[56] References Cited

U.S. PATENT DOCUMENTS

| | | | |
|---|---|---|---|
| 2,627,855 | 2/1953 | Price | 606/67 |
| 2,834,342 | 5/1958 | Yost | 606/67 |
| 3,002,514 | 10/1961 | Deyerle | 606/67 |
| 3,025,853 | 3/1962 | Mason | 606/67 |
| 3,029,811 | 4/1962 | Yost | 606/67 |
| 3,561,437 | 2/1971 | Orlich | 606/67 |
| 4,103,683 | 8/1978 | Neufeld | 606/67 |
| 4,628,923 | 12/1986 | Medoff . | |
| 4,776,330 | 10/1988 | Chapman et al. . | |
| 4,908,032 | 3/1990 | Keller | 623/16 |
| 4,978,349 | 12/1990 | Frigg | 606/67 |
| 5,002,544 | 3/1991 | Klaue et al. | 606/69 |
| 5,032,125 | 7/1991 | Durham et al. | 606/62 |
| 5,047,029 | 9/1991 | Aebi et al. | 606/61 |
| 5,116,336 | 5/1992 | Frigg | 606/65 |
| 5,295,991 | 3/1994 | Frigg | 606/62 |
| 5,300,074 | 4/1994 | Frigg . | |
| 5,312,402 | 5/1994 | Schläpfer et al. | 606/53 |
| 5,437,666 | 8/1995 | Tepic et al. | 606/55 |
| 5,462,547 | 10/1995 | Weigum | 606/65 |
| 5,498,264 | 3/1996 | Schlapfer et al. | 606/72 |
| 5,501,684 | 3/1996 | Schlapfer et al. | 606/73 |
| 5,534,001 | 7/1996 | Schlapfer et al. | 606/61 |
| 5,591,168 | 1/1997 | Judet et al. | 606/65 |

OTHER PUBLICATIONS

Richards et al., "The AO Dynamic HIP Screw and the Pugh Sliding Nail in Femoral Head Fixation," J. Bone Joint Surg. [Br] 72-B:794-6, (1990).

Jarrett et al., "The stable internal fixation of peritrochanteric hip fractures," Part V (pp. 203-218).

Calandruccio et al., "Internal Fixation Devices for Fractures of the Proximal Femur American Academy of Orthopaedic Surgeons Committee on the History of Orthopaedic Surgery," Brochure (pp. 1-7).

William K. Massie, M.D., "Extracapsular Fractures of the Hip Treated by Impaction Using a Sliding Nail-plate Fixation," Chapter 18 (pp. 180-201).

"The Titanium Unreamed Femoral Nail System Technique Guide", 1995 Synthes (USA).

*Primary Examiner*—Guy V. Tucker
*Attorney, Agent, or Firm*—Pennie & Edmonds LLP

[57] ABSTRACT

An osteosynthetic implant for setting a broken bone. The implant comprises a nail having a plurality of helically twisted blades that share a common helical axis. At least two of the blades define an angle of less than 180° in a plane perpendicular to the helical axis. In a preferred embodiment, one pair of the blades of the nail is tapered towards its proximal portion and another pair has a uniform thickness. The blades are twisted by at least about 30°. A cannulation runs through the center of the nail to receive a guide wire. The nail is slidably engageable to a member that is securable to an elongated portion of the bone, such as a side plate or an intramedullary nail. In a preferred implantation orientation, the proximate portion of the tapered blades is parallel to the elongated portion of the bone, and a proximate portion of the uniform blades is perpendicular thereto.

26 Claims, 5 Drawing Sheets

5,741,256

1

HELICAL OSTEOSYNTHETIC IMPLANT

TECHNICAL FIELD

The invention relates to an implant for setting bone fractures and in particular to an implant for osteosynthesis of stable and unstable fractures of the neck and intertrochanteric region of the femur.

BACKGROUND OF THE INVENTION

The elderly population experiences a high incidence of femoral fractures, commonly in the femoral neck and intertrochanteric regions. These fractures are normally treated by inserting a nail or hip screw from the side of the femur, through the neck, and into the femoral head. The nail or screw is then fixed to a side plate, that is fastened to the outside of the femur shaft, or to an intramedullary nail, that is inserted through the femur shaft. Both the side plate and the intramedullary nail may by secured to the femur shaft with bone screws.

A high incidence of death, between 10% to 25%, is associated with this type of hip fractures due to the injury itself or related complications. Frequent complications may arise when two or more bone fragments are forced towards each other when the patient supports his or her weight on the healing bone. For example, an sharp implanted nail or hip screw may cut through and penetrate the femoral head or neck; or a nail, hip screw, side plate, or intramedullary nail may bend or break under load where the contact between bone fragments is insufficient for the bone itself to carry the patient's weight.

Collapsible implants have been developed to maximize bone to bone contact by permitting bone fragments to migrate towards one another. Examples in the prior art include the Richards-type compression hip-screw and the Kenn-type nail. Richards screws comprise a long, smooth shaft and external threads at the tip. Kenn nails comprise a wide, tri-flanged tip at the end of a smooth shaft. In both examples, the nail or screw implanted through the neck of the femur is allowed to slide back through the side plate or intramedullary nail as the bone fragments move together under a load.

On the other hand, these known implants are laterally stiff. Their sharp ends may cut sideways through the cancellous tissue of a femoral head after implantation and migrate within the bone, either piercing the surface of the femur or simply no longer retaining proper alignment of bone fragments. To resolve this problem, single, helical blades were developed, such as the SPIRAL BLADE brand, currently sold by Synthes, Paoil, Pa., and such as disclosed in U.S. Pat. Nos. 5,300,074 and 4,978,349. These blades are twisted about 90° along their length and have a substantially uniform width. When implanted into the neck and head of a femur, the distal end of the blade lies in parallel with the femur shaft, and the proximal end lies perpendicularly to the shaft. In this position, the load on the head acts on relatively flexible, large, flat surface, reducing the pressure on the cancellous tissue and diminishing the tendency of the implant to further cut through the bone once implanted. The distal end, being aligned with the femoral shaft, provides a higher bending stiffness than the tip to sufficiently support the blade. Also, unlike previous nails and screws, these blades require little or no material removal in the femoral head, prior to implantation, where the amount of bone is critical.

These single, helical blades, however, are fairly compliant in the transverse direction, towards the fore and aft of the patient's body, because of the vertical positioning of the distal end of the blade. Moreover, the blades provide little resistance to cutting through the cancellous bone like a knife in directions aligned with the width of the blade at any station along its length. A need exists, therefore, to provide improved osteosynthetic implants which do not have a tendency to cause such cutting.

SUMMARY OF THE INVENTION

The invention relates to a dynamic osteosynthetic-implant that minimizes the tendency to cut through the cancellous bone tissue after implantation and provides the required stiffness to maintain the relative orientation of the bone fragments. One implant according to the invention includes a plurality of helically twisted blades fixed to one another along a common helical axis. At least two of the blades define an angle of less than 180° in a plane disposed perpendicularly to the helical axis. The blades are preferably slidably engageable to a first member, such as a side plate or an intramedullary nail, that is itself engageable to the shaft of a femur. These blades provide the implant with a relatively flexible, large area, proximal end, but which gradually becomes stiffer towards its distal portion for additional support.

In a preferred embodiment, two perpendicular pairs of oppositely oriented blades are helically twisted by at least about 30°. One pair of blades tapers towards its proximal end; the other pair has substantially uniform widths. In a preferred implanted orientation, the distal ends of the uniform blades are oriented in parallel to the femoral shaft, while the distal ends of the tapered blades are oriented perpendicularly to the shaft. The respective proximal ends are oriented at about 90° of helical twist to their distal ends. As a result, the proximal end of the implant provides a large surface normal to the principal downward load on the head of the femur and is more compliant than the distal portion of the implant, with the distal portion having increased bending stiffness in all directions. Moreover, the angle formed between any two adjacent blades, together with the portions of the blades normal to a shearing load on the bone, resist the tendency of the implant to cut out through the bone under such a load.

DETAILED DESCRIPTION OF THE PREFERRED EMBODIMENTS

Figure 1:
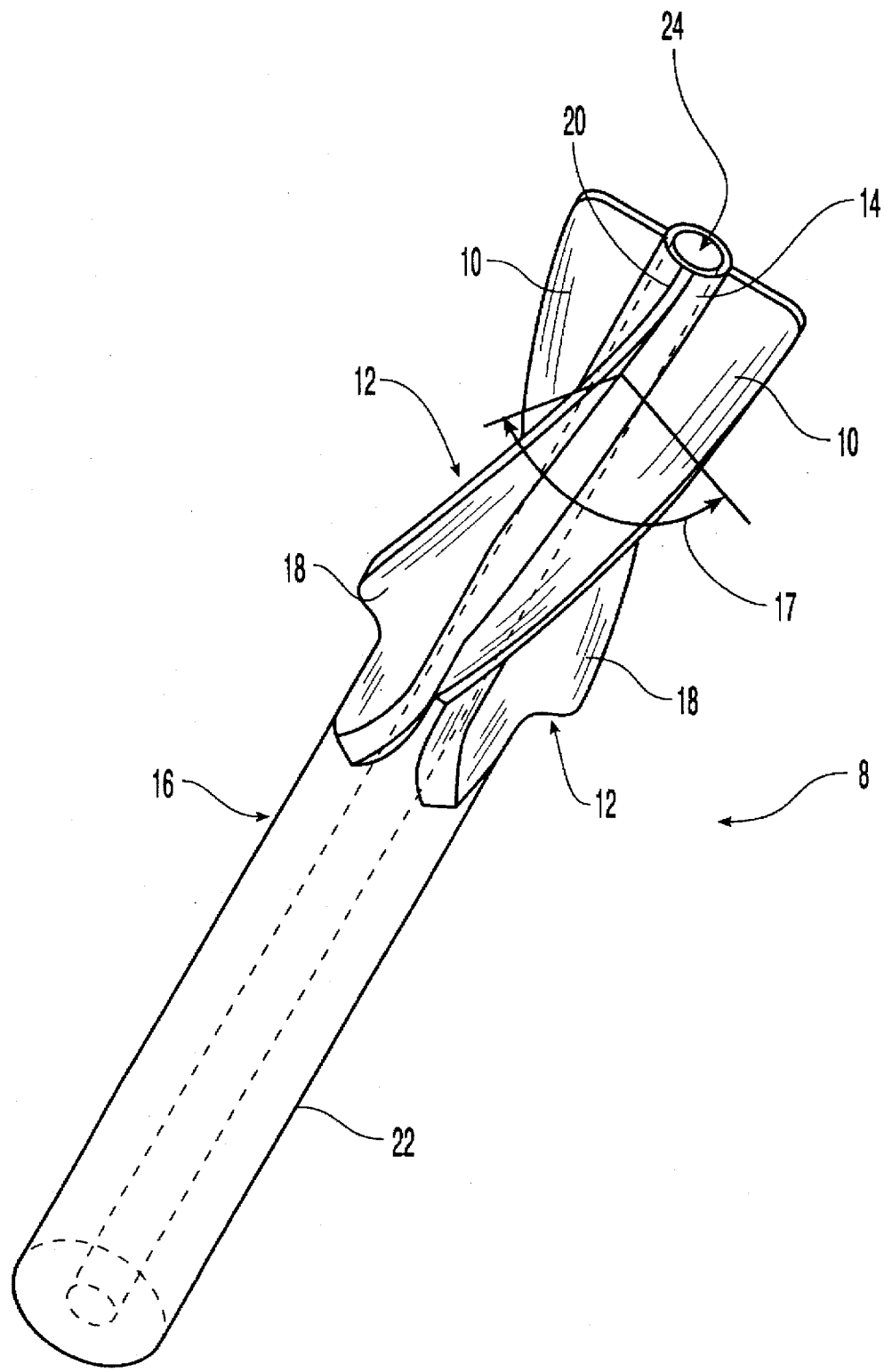
FIG. 1 is a perspective view of a preferred embodiment of an implant according to the invention.

Referring to FIG. 1, an osteosynthetic nail 8 comprises a plurality of helically twisted blades 10 and 12 that are fixed to a proximal portion 14 of a shaft 16. In this description of the preferred embodiments, the terms distal and proximal are defined in relation to a surgeon implanting the device. Thus, a proximal portion of an element is preferably located closer to the central part of the body than its distal portion. The shaft 16 is coaxial with the common helical axis of the blades 10 and 12. The blades 10 and 12 are substantially flat and may have sharp proximal ends. Their helical twist is at least about 30°, preferably from about 45° to 120° and most preferably about 90°. The helical rate of twist is such that nail 8 may be driven into a femur from the distal end of the nail 8. After implantation, this twist also inhibits nail 8 from sliding forwards or backwards along its helical axis with respect to the femoral head.

The preferred embodiment comprises a pair of uniform blades 10 disposed on opposite sides of the helical axis and exhibiting a substantially uniform width, and a tapered pair of blades 12 disposed on opposite sides of the helical axis and substantially at right angles to the uniform blades 10. The angle 17, defined between at least two adjacent blades at any station along the helix, may be any angle of less than 180°. Preferably, this angle is between 30° and 150°, and more preferably between 60° and 120°. The most preferable angle when four blades are used is 90°. The tapered blades 12 are widest at their distal ends 18 and taper down, in the direction of their proximal ends 20, until they lie flush with the outer surface of the proximal portion 14 of the shaft 16. Only one of the two proximal ends 20 of the blades 12 is visible in FIG. 1. From this vantage, the other is hidden behind the shaft 16.

A cannulation 24 extends along the inner length of shaft 16. The cannulation 24 is sized to permit the insertion of a guide wire (not shown) to aid in the alignment of the nail during the implantation procedure as is commonly known in the art.

Figure 2:
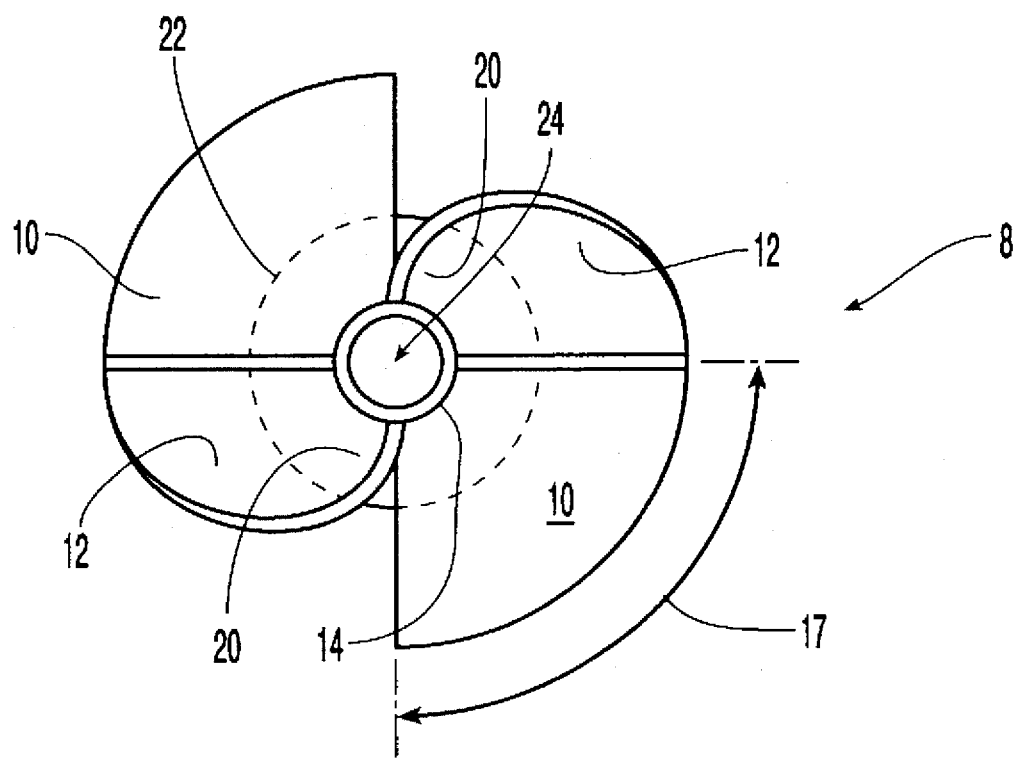
FIG. 2 shows a proximal view of an implant according to the invention.

FIG. 2 is a view from the proximal end of the nail which illustrates the helical shape of blades 10 and 12 and the taper of blades 12. It also shows the angle 17 formed between the blades 10 and 12. From this view, the distal ends 18 of the tapered blades 12 are directly behind the proximal tips of the uniform blades 10 and are thus hidden from view.

Figure 3:
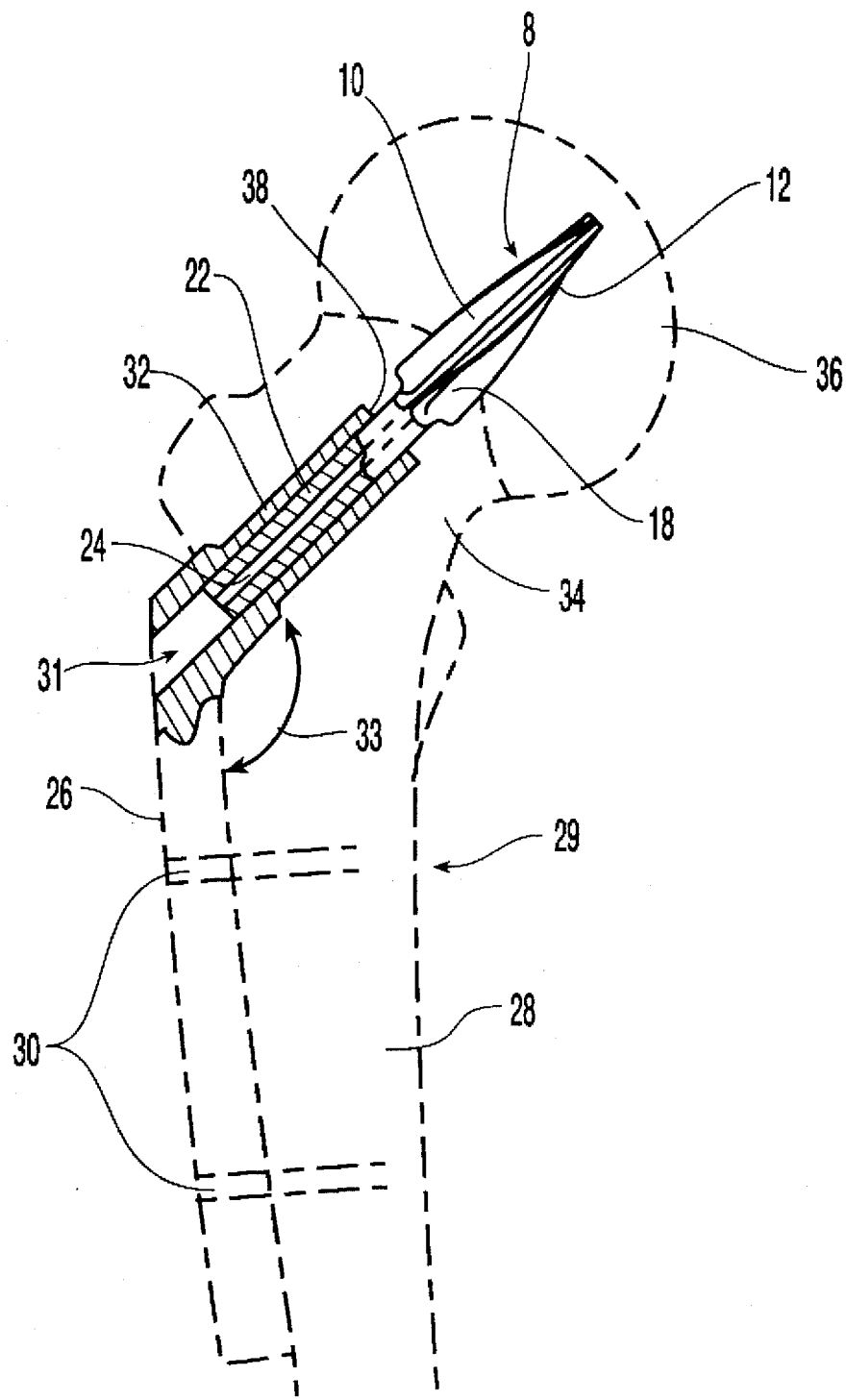
FIG. 3 is cross-sectional side-view of an implant according to the invention implanted in a femur in conjunction with a side plate.

In FIG. 3, an embodiment that employs a side plate 26 is shown in a preferred implantation orientation. Side plate 26 is aligned with the shaft 28 of femur 29 and is securable to the outside thereof with fasteners 30, as shown in FIG. 3. A portion of the side plate 26, in one embodiment, may slide vertically with respect to fasteners 30 to allow for vertical compression of the bone fragments. The proximal portion 22 of shaft 16 is telescopically slideable within a and denoting a helical phase difference between the adjacent blades cylindrical sleeve 32 that is fixed to the side plate 26 at an angle 33 that will be generally between 90° and 150°, but that may be selected according to the anatomy of the patient. Alternatively, the side plate may be configured and dimensioned as a fixed plate that does not vertically move with respect to the fasteners. The length, width and other dimensions of either the fixed or slidable plate can be selected by one of ordinary skill in the art.

The implantation procedure for fixation nails is also well known in the art and can be applied with the present invention. In the preferred implantation orientation, sleeve 32 penetrates the side of the femur 29 towards the femur neck 34 and head 36. The distal portion 22 of shaft 16 in this embodiment has a larger outer diameter than does the proximal portion 14. This distal portion 22 is slidably engaged within sleeve 32 such that the distal ends of blades 10 and 12 are separated from the proximal end 38 of the sleeve. This separation enables the nail 8 to slide back into the sleeve 32 as the femur head 36 is compressed distally in the direction of the helical axis. This prevents the blades 10 and 12 from further cutting the head 36 after implantation.

The nail 8 is implanted inside the neck 34 and head 36 of the femur 29. The distal portions of the uniform blades 10 are oriented in parallel to the shaft 28 of the femur, while the distal portions 18 of the tapered blades 12 are perpendicular to the femur shaft 28. At their proximal ends, uniform blades 10 are perpendicular to the femur shaft while tapered blades 12 and proximal ends 20 are parallel to the femur shaft 28.

In this orientation, the wide proximal portions of the uniform blades 10 provides a large surface normal to the principal downward load imposed on the femoral head 36 when the patient stands and ambulates. This reduces the pressure on the cancellous tissue within the femur 29 and resists the tendency to cut through the bone cortex. The distal portions of the uniform blades 10, aligned with the principal load, increase the bending stiffness of the shaft 16 resisting that load, and efficiently transfer the load to the side plate 26. The taper in the tapered blades 12 affords additional stiffness in their distal portions 18, where blades 12 have a larger width, but retains the compliancy of the nail 8 at the tapered proximal ends 20. In this manner, the proximal part of the nail 8 may flex, rather than carve through, or crush, the bone tissue. In addition, the extra surface area furnished by tapered blades 12 also counter any propensity of the blades 10 and 12 to migrate laterally relative through the bone 29. Moreover, if the nail 8 is forced laterally into the bone tissue, the tissue will be driven into the angles formed between adjacent blades 10 and 12, further resisting nail 8 migration. Preferably, the outer diameter of sleeve 32 is about the size of the widest portion of nail 8 so that nail 8 may fit easily through a hole drilled for insertion of the sleeve 32, making it easier to achieve the above orientation.

Figure 4:
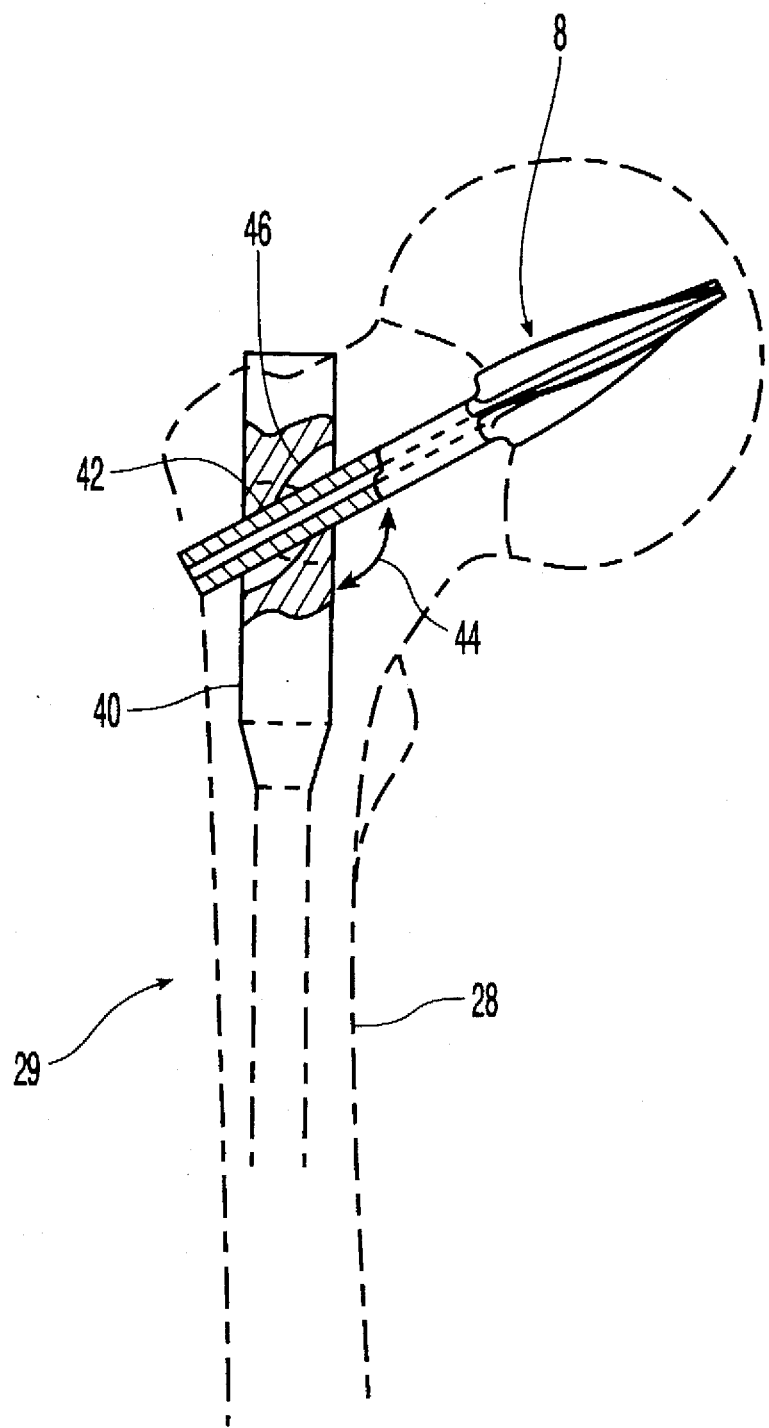
FIG. 4 illustrates a cross-sectional side-view of an implant according to the invention implanted in a femur in conjunction with an intramedullary nail.
Figure 5:
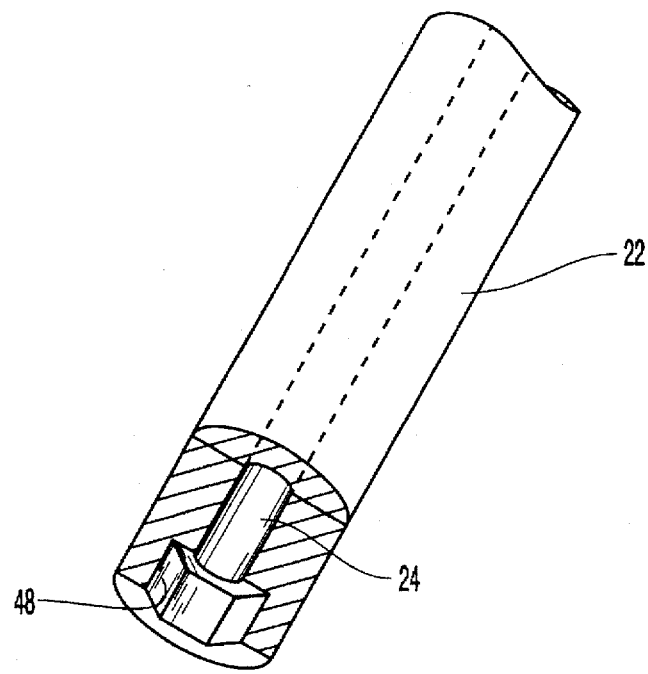
FIG. 5 is a partial cross-section of a perspective of an alternative embodiment of the implant.
Figure 6:
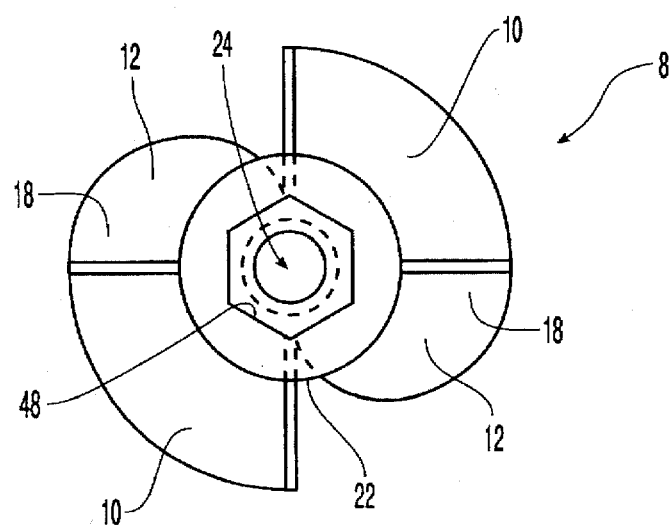
FIG. 6 is a distal view of the embodiment shown in FIG. 5.

An alternative embodiment is shown in FIG. 4. This embodiment utilizes an intramedullary nail 40 implanted in the femoral shaft 28. As in the first embodiment described, the nail 6 may slide telescopically within a channel 42 inside the intramedullary nail 40. The channel 42 defines an angle 44 with the length of the intramedullary nail 40 of generally between 90° and 150°, which may be chosen according to shape of the femur.

During implantation, the intramedullary nail 40 is inserted into the bone first. The nail 8 is then implanted through the side of the femur 29 through a hole drilled merely up to the depth of the side surface of the intramedullary nail 40. Helical groves 46 extend radially from channel 42 and are shaped to receive blades 10 and 12. As the nail 8 is hammered into the bone, as commonly done by persons skilled in the art, blades 10 and 12 slide through grooves 46.

The preferred implantation orientation resembles that of the side-plate embodiment. The nail 8 is positioned in the same relationship to the femur 29 and shares the same advantages.

In another embodiment, with which either a side plate or an intramedullary nail may be employed, the distal end of the nail 8 defines a hexagonal cavity 48 concentric with the proximal base of the shaft 16 and the cannulation 24. This cavity 48 is shaped to receive the tip of an instrument, normally used in the art, designed to ease rotational orientation of the nail during implantation. The cavity 48 may be shaped differently depending on the instrument used. For, example, instead of a central cavity, the distal base and sides of shaft 16 may have indentations or raised portions to fit the instrument.

The length and proportions of the elements of the invention may be selected by the surgeon according to the anatomy of the patient. Examples of selectable dimensions include the length of nails 8 and sizes of side plate 26 or intramedullary nail 40. Also, other embodiments may contain a different number of blades, if desired.

It will be appreciated that those skilled in the art may devise numerous modifications and embodiments. It is intended that the following claims cover all such modifications and embodiments that fall within the true spirit and scope of the present invention.

I claim:

1. An implant for setting a broken bone comprising:

a nail for implantation in a bone fragment and having first and second blades which are helically twisted along first and second coaxial helixes respectively, the first and second coaxial helixes being less than 180° out of phase, with the second blade being tapered and having a proximal portion and a distal portion that is wider than the proximal portion; and a securing member being securable to an elongate portion of the bone, said nail being engageable to said securing member.

2. The implant of claim 1, wherein said blades are substantially flat and the helixes are out of phase by between 30° and 150°.

3. The implant of claim 1, wherein the helixes are out of phase by between 60° and 120°.

4. The implant of claim 1, wherein said blades are twisted by at least about 30° along said helixes.

5. The implant of claim 1, wherein the second blade is twisted by about 45° to 120° along the second helix.

6. The implant of claim 5, wherein the second blade is twisted by about 90° and said nail may be implanted such that the proximal width of the second blade is parallel to the elongate portion of the bone.

7. The implant of claim 1, wherein the nail is operatively associated with the securing member to facilitate substantially axial sliding movement of the nail as the bone fragment compresses towards the elongate portion of the bone.

8. The implant of claim 1, wherein the nail is axially slideably engageable to the securing member for permitting compression of bone fragments.

9. The implant of claim 8, further comprising a telescoping portion of the nail which is telescopically engageable to the securing member.

10. The implant of claim 9, wherein said securing member comprises a sleeve for receiving said telescoping portion.

11. The implant of claim 10, wherein:

said sleeve comprises an outer sleeve diameter; and said blades define a helical diameter which is at most about as large as said outer sleeve diameter.

12. The implant of claim 8, wherein said securing member has a channel for receiving the nail defining helical grooves extending from an inside portion of the channel and being aligned therewith, said blades being slideable within the groves.

13. The implant of claim 1, further comprising a hollow shaft for receiving a guide wire, said hollow shaft extending coaxially with the helixes.

14. The implant of claim 1, wherein said securing member is securable to an outside portion of the elongate portion of the bone.

15. The implant of claim 1, wherein said securing member comprises an intramedullary nail for insertion within the elongate portion of the bone.

16. The implant of claim 1, wherein said securing member and an axis that is coaxial with the helixes define an angle of between about 90° and 150°.

17. The implant of claim 1, wherein the nail comprises third and fourth blades being helically twisted along third and fourth helixes respectively, the third and fourth helixes being out of phase with each other and coaxial with the first and second helixes, wherein the fourth blade is tapered.

18. The implant of claim 17, wherein the second and fourth blades are respectively positioned between the first and third blades on opposite sides of the nail.

19. The implant of claim 1, wherein the first blade has a substantially uniform width along the first helix.

20. The implant of claim 1, wherein the blades are coextensive over at least a portion of the first and second helixes.

21. The implant of claim 1, wherein the first and second helixes are about 90° out of phase.

22. An implant for setting a broken bone, the implant comprising:

a securing member securable to an elongate portion of the bone; and a nail having a shaft defining a helical axis, a uniform pair of blades disposed on the shaft, and a tapered pair of blades disposed on the shaft in a manner such that each tapered blade is positioned between the uniform pair of blades, said tapered blades having a greatest width at a distal portion and a smallest width at a proximal portion, said uniform and tapered blades having a total helical twist of at least about 30° around the helical axis;

wherein the nail is engageable to the securing member.

23. The implant of claim 22, wherein each tapered blade is about 90° out of helical phase with the uniform blades.

24. The implant of claim 22, wherein the uniform blades are disposed substantially on opposite sides of the helical axis, and the tapered blades are disposed substantially on opposite sides of the helical axis.

25. A method of setting a broken femur having a head and a shaft, the method comprising:

implanting a nail into the femur, the nail having a helical axis, a uniform pair of blades disposed on the helical axis, and a tapered pair of blades disposed on the helical axis in a manner such that each tapered blade is positioned between the uniform pair of blades, said tapered blades having a greatest width at a distal portion and a smallest width at a proximate portion, said uniform and tapered blades having a total helical twist of at least about 30° around the helical axis, wherein the proximate portion of said tapered blades is implanted inside the head of the femur and substantially in parallel to the shaft of the femur, and the distal portion of said tapered blades is disposed away from the head of the femur and substantially perpendicularly to the shaft of the femur;

securing a securing member to the shaft of the femur; and slidably engaging said nail to said securing member such that fragments of the femur can migrate towards each other.

26. An implant for setting a broken bone comprising:

a nail for implantation in a bone fragment and having a plurality of blades helically twisted along a common helical axis and being less than 180° out of helical phase; and a securing member being securable to an elongate portion of the bone and configured for receiving the nail and preventing obstruction of movement of the nail substantially along the helical axis as the bone fragment compresses towards the elongate portion of the bone.

* * * * *